United States Patent [19]

Brown et al.

[11] 4,255,428

[45] * Mar. 10, 1981

[54] 5-(HYDROXYPYRIDYLALKYL)-4-PYRIMI-DONES

[75] Inventors: Thomas H. Brown; Graham J. Durant, both of Welwyn Garden City; Charon R. Ganellin, Welwyn, all of England

[73] Assignee: Smith Kline & French Laboratories Limited, Welwyn Garden City, England

[*] Notice: The portion of the term of this patent subsequent to May 15, 1996, has been disclaimed.

[21] Appl. No.: 32,979

[22] Filed: Apr. 24, 1979

[30] Foreign Application Priority Data

Mar. 24, 1979 [GB] United Kingdom ............... 10424/79

[51] Int. Cl.$^3$ ................. A61K 31/505; C07D 401/14; C07D 417/14
[52] U.S. Cl. .................................... 424/251; 544/320; 546/304; 546/296; 546/297; 546/301; 546/339; 546/348; 548/134; 548/138; 548/203; 548/146; 548/206; 548/214; 548/337; 548/341
[58] Field of Search .......................... 544/320; 424/251

[56] References Cited

U.S. PATENT DOCUMENTS

| 3,980,781 | 9/1976 | Snell et al. ............................. 424/251 |
| 4,145,546 | 3/1979 | Brown et al. .......................... 544/320 |
| 4,153,793 | 5/1979 | Durant et al. .......................... 544/320 |
| 4,154,834 | 5/1979 | Brown et al. .......................... 544/320 |

FOREIGN PATENT DOCUMENTS 849810 6/1977 Belgium .
1223686 3/1971 United Kingdom .

Primary Examiner—Donald G. Daus
Assistant Examiner—James H. Turnipseed
Attorney, Agent, or Firm—Joan S. Keps; Richard D. Foggio; Alan D. Lourie

[57] ABSTRACT

The compounds are substituted 2-amino-4-pyrimidones with a 5-(hydroxypyridylalkyl) substituent which are histamine $H_2$-antagonists. Two specific compounds are 2-[2-(3-bromo-2-pyridylmethylthio)ethylamino]-5-(2-hydroxy-4-pyridylmethyl)-4-pyrimidone and 2-[4-(3-methoxy-2-pyridyl)butylamino]-5-(2-hydroxy-4-pyridylmethyl)-4-pyrimidone.

13 Claims, No Drawings

5-(HYDROXYPYRIDYLALKYL)-4-PYRIMIDONES

This invention relates to pharmacologically active pyrimidone derivatives, a process for preparing them, and pharmaceutical compositions containing them.

According to the present invention there is provided a pyrimidone of Structure (1)

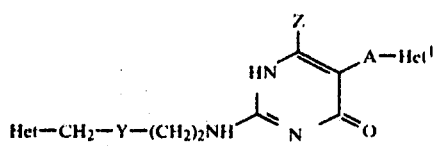

(1)

in which Het is a 2- or 4- imidazolyl group optionally substituted by lower alkyl (preferably methyl), halogen (preferably chlorine or bromine), trifluoromethyl or hydroxymethyl, a 2-pyridyl group optionally substituted by one or more (which can be the same or different) lower alkyl (preferably methyl), lower alkoxy (preferably methoxy), halogen (preferably chlorine or bromine), amino or hydroxy groups, a 2-thiazolyl group, a 3-isothiazolyl group optionally substituted by chlorine or bromine, a 3-(1,2,5)-thiadiazolyl group optionally substituted by chlorine or bromine, or a 2-(5-amino-1,3,4-thiadiazolyl) group; Y is sulphur or methylene; Z is hydrogen or lower alkyl (preferably methyl); A is $C_1$-$C_5$ alkylene; and Het[1] is a pyridyl group substituted by hydroxy and optionally substituted by lower alkyl or lower alkoxy. The compounds of Structure (1) can be in the form of the free bases or their pharmaceutically acceptable acid addition salts.

Throughout this specification by the terms 'lower alkyl' and 'lower alkoxy' is meant alkyl and alkoxy groups containing 1 to 4 carbon atoms which can be straight or branched. Particular lower alkyl groups are methyl, ethyl, 1-propyl and 2-propyl. Particular lower alkoxy groups are methoxy, ethoxy, 1-propoxy and 2-propoxy.

Preferably Het is a 5-methyl-4-imidazolyl, 5-bromo-4-imidazolyl, 2-pyridyl, 3-methyl-2-pyridyl, 3-methoxy-2-pyridyl, 3-ethoxy-2-pyridyl, 3,4-dimethoxy-2-pyridyl, 3-fluoro-2-pyridyl, 3-chloro-2-pyridyl, 3-bromo-2-pyridyl, 3-iodo-2-pyridyl, 3-bromo-4-methyl-2-pyridyl or 2-thiazolyl group.

Preferably Z is hydrogen.

Preferably A is straight α,ω-alkylene, parricularly methylene.

Particular meanings of Het[1] are 4-hydroxy-2-pyridyl, 6-hydroxy-3-pyridyl, 2-hydroxy-4-pyridyl, 4-hydroxy-5-methyl-2-pyridyl, 6-hydroxy-5-methyl-3-pyridyl, 2-hydroxy-6-methyl-4-pyridyl and 6-hydroxy-5-methoxy-3-pyridyl.

Preferably Het[1] is 4-hydroxy-2-pyridyl, 6-hydroxy-3-pyridyl or 2-hydroxy-4-pyridyl.

A particular group of compounds of Structure (1) is that in which Het[1] is a pyridyl group substituted by hydroxy.

The compounds of the invention are shown and described as 4-pyrimidones and these exist in equilibrium with the corresponding 6-pyrimidones, and to a lesser extent in the following tautomeric forms:

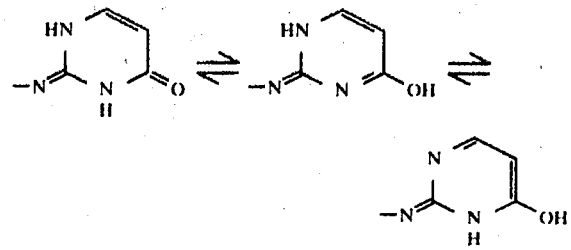

The 2-,4- and 6-hydroxypyridyl groups can exist as 1H-pyridone tautomers, and certain of the Het groups can exist in several tautomeric forms. All these tautomeric forms of the compounds of Structure 1 are within the scope of the present invention.

In a process of the invention a compound of Structure (1) is prepared by reacting a compound of Structure (3);

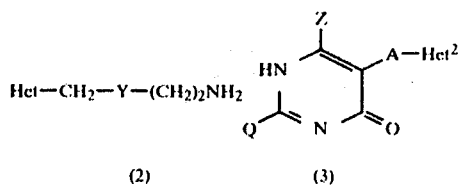

(2)    (3)

in which Q is nitroamino ($NO_2NH$—), lower alkylthio, benzylthio, chlorine, bromine or other group which can be displaced with a primary amine, Z and A are as defined for Structure (1), and Het[2] is a pyridyl group substituted by hydroxy or a protected hydroxy group and optionally substituted by lower alkyl or lower alkoxy, with an amine of Structure (2), in which Het and Y are as defined for Structure (1) and removal of any hydroxy protecting groups.

This reaction can be carried out at an elevated temperature in the absence of a solvent, for example at 80° to 170° preferably 120° to 140°, or in a solvent at an elevated temperature, for example at the reflux temperature of the reaction mixture. The choice of solvent is affected by solubility characteristics of the reactants and the particular meaning of Q. Preferably the solvent is pyridine, a picoline or mixture of picolines, a lower alkanol, preferably ethanol or 1-propanol, an aqueous mixture of a lower alkanol, 1,2-ethanediol, a ketone, for example acetone or 2-butanone, or a polar aprotic solvent for example dimethylformamide, dimethylacetamide, dimethylsulphoxide, hexamethylphosphoramide, sulpholane, acetonitrile or nitromethane. Particularly preferably Q is nitroamino and the reaction is carried out in refluxing ethanol, refluxing 1-propanol or refluxing pyridine, or Q is methylthio and the reaction is carried out in refluxing pyridine.

Preferably approximately equimolar amounts of the reactants are used, although an excess for example a slight excess of from 1.1 to 1.5 molar equivalents or a larger excess of from 1.5 to 4 molar equivalents, of either reactant can be used. If an excess of a reactant is used then preferably an excess of the amine of Structure (2) is used. An excess of either reactant can be present at the start of the reaction or can be added during the course of the reaction.

Examples of hydroxy protecting groups are methoxymethyl, methylthiomethyl, tetrahydropyranyl, arylmethyl, for example benzyl, lower alkyl, for example methyl, and acyl, for example formyl or acetyl. Compounds of Structure (1) in which Het¹ is a 2-, 4-, or 6-hydroxypyridyl group can be conveniently prepared from a compound of Structure (3) in which Het² is a pyridyl group with a 2-, 4-, or 6-lower alkoxy substituted by acid hydrolysis of the product of the reaction with an amine of Structure (2).

The compounds of Structure (3) in which Q is nitroamino can be prepared by reacting a β-oxoester of Structure (4)

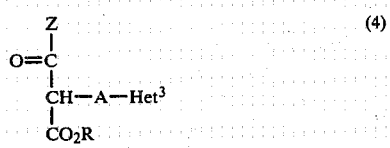

in which Z is hydrogen or lower alkyl, R is lower alkyl, A is as defined for Structure (1), and Het³ is a pyridyl group substituted by hydroxy or a protected hydroxy group, and optionally substituted by lower alkyl or lower alkoxy, with nitroguanidine, and optionally removing any hydroxy protecting group present.

The compounds of Structure (3) in which Q is lower alkylthio or benzylthio can be prepared by reacting a β-oxoester of Structure (4) in which Het³ is a pyridyl group substituted by hydroxy, or a protected hydroxy group, and optionally substituted by lower alkyl or lower alkoxy, with thiourea, and alkylating or benzylating the 2-thiouracil formed, and optionally removing any hydroxy protecting group present.

The compounds of Structure (3) in which Q is chlorine or bromine can be prepared by reacting a β-oxoester of Structure (4) with guanidine and diazotising the product in hydrochloric acid in the presence of cuprous chloride or in hydrobromic acid in the presence of cuprous bromide, and optionally removing any hydroxy group present.

Preferably the reactions of the β-oxoester of Structure (4) with nitroguanidine, thiourea and guanidine are carried out in the presence of a base, for example, an alkali metal lower alkoxide, preferably sodium methoxide or sodium ethoxide, an alkali metal carbonate or hydroxide, preferably potassium carbonate or sodium hydroxide, sodium hydride or a quarternary ammonium hydroxide, for example benzyltrimethyl-ammonium hydroxide. Preferably this reaction is carried out at an elevated temperature, for example the reflux temperature of the solvent mixture. Preferably the solvent is a lower alkanol, for example ethanol, an aqueous mixture of a lower alkanol, a ketone, for example 2-butanone, or a polar aprotic solvent, for example dimethylformamide. When Z is hydrogen the β-oxoester of Structure (4) can be used in the form of a hemiacetal of a lower alkanol.

The amines of Structure (2) in which Y is sulphur can be prepared by reacting cysteamine with a compound of formula Het—CH₂L where L is a group displaceable with a thiol, for example hydroxy, acyloxy (for example acetoxy, methanesulphonyloxy or p-toluenesulphonyloxy), lower alkoxy (for example methoxy), chlorine, bromine or triarylphosphonium (for example triphenylphosphonium). Preferably L is hydroxy or methoxy and the reaction is carried out under acidic conditions, for example in hydrochloric or hydrobromic acid.

The amines of Structure (2) in which Y is methylene and Het is a 2-pyridyl group with a lower alkoxy group or halogen atom in the 3-position can be prepared by reacting a 2-halo-3-nitropyridine with diethyl 2-(2-cyanoethyl)-malonate. Hydrolysis and decarboxylation of the product followed by reduction with palladium and charcoal gives a 3-amino-3-(3-cyanopropyl)pyridine which can be diazotised in 2M sulphuric acid and alkylated in dimethyl sulphoxide to give a 3-alkoxy-2-(3-cyanopropyl)pyridine. The 3-amino-2-(3-cyanopropyl)-pyridines can be reduced with lithium aluminium hydride to give a 4-(3-amino-2-pyridyl)-butylamine which can be diazotised in strong hydrochloric acid in the presence of cuprous chloride to give a 3-chloro amine, or diazotised in strong hydrobromic acid in the presence of cuprous bromide to give a 3-bromo amine, or diazotised in dilute sulphuric acid containing sodium iodide to give a 3-iodo amine. The 3-amino-2-(3-cyanopropyl)pyridines can be diazotised in fluoroboric acid and reduced with lithium aluminium hydride to give a 4-(3-fluoro-2-pyridyl)butylamine.

The amines of Structure (2) in which Y is methylene and Het is a 2-thiazolyl group can be prepared by reacting a thioamide of structure $NH_2CS(CH_2)_4Q$ where Q is a protected amino group with a dialkyl acetal of bromoacetaldehyde and removal of the amino-protecting group.

The esters of Structure (4) can be prepared by alkylating a dialkyl malonate followed by hydrolysis and decarboxylation, or by condensing an aldehyde with malonic acid and decarboxylating, esterifying and reducing the product.

The compounds of Structure (1) have histamine H₂-antagonist activity and also have histamine H₁-antagonist activity and are particularly active as histamine H₂-antagonists when compared to analogous compounds in which Het¹ is other than a pyridyl ring substituted by hydroxy. The compounds of Structure (1) also have a low lipophilicity as measured by octanol-water distribution.

In this specification by histamine H₂-receptors is meant receptors defined by Black et al. (Nature, 236, 385 (1972)) as those histamine receptors which are not blocked by mepyramine but are blocked by burimamide, and by histamine H₁-receptors is meant receptors involved in mepyramine-sensitive histamine responses. Compounds which block histamine H₂-receptors are referred to as histamine H₂-antagonists and compounds which block histamine H₁-receptors are referred to as histamine H₁-antagonists.

Blockade of histamine H₂-receptors is of value in inhibiting the biological actions of histamine which are not inhibited by histamine H₁-antagonists. Histamine H₂-antagonists are active, for example, as inhibitors of gastric acid secretion, as antiinflammatory agents and as agents which act on the cardiovascular system, for example as inhibitors of the effects of histamine on blood pressure.

In some physiological conditions the biological actions of histamine are mediated through both histamine H₁- and H₂-receptors and blockade of both types of receptors is useful. These conditions include inflammation mediated by histamine, for example skin inflammation, and those hypersensitivity responses due to the action of histamine at H₁- and H₂-receptors, for example allergies.

The activity of the compounds of Structure (1) as histamine H₂-antagonists can be demonstrated by the inhibition of histamine-stimulated secretion of gastric acid from the lumen-perfused stomachs of rats anaesthetised with urethane, at doses of less than 16 micromoles per kilogram intravenously. This procedure is referred to in Ash and Schild, Brit. J. Pharmac. Chemother. 27, 427 (1966). Their activity as histamine $H_2$-antagonists can also be demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus. They inhibit the basal secretion of gastric acid and also that stimulated by pentagastrin or by food. In a conventional test such as the measurement of blood pressure in the anaesthetised cat, at doses of from 0.5 to 256 micromoles per kilogram intravenously they inhibit the vasodilator action of histamine. The potency of these compounds is illustrated by the effective doses producing 50% inhibition of gastric acid secretion in the anaesthetised rat and the dose producing 50% inhibition of the histamine-induced tachycardia in the isolated guinea pig atrium (less than $10^{-4}$ Molar). The activity of the compounds of Structure (1) as histamine $H_1$-antagonists can be demonstrated by the inhibition of histamine-stimulated contractions of the isolated guinea-pig ileum. It is advantageous to administer a single compound having histamine $H_1$- and $H_2$-antagonist activity rather than to administer individual compounds having histamine $H_1$-antagonist activity and histamine $H_2$-antagonist activity as difficulties arising from differing rates of absorption and pharmacokinetic characteristics are avoided.

The pharmaceutical compositions of the invention comprise a pharmaceutical carrier and a pharmacologically active compound of Structure (1)which can be in the base form or in the form of an addition salt with a pharmaceutically-acceptable acid. Such addition salts include those with hydrochloric, hydrobromic, hydriodic, sulphuric and maleic acids and may conveniently be formed from the corresponding compounds of Structure (1) by standard procedures, for example by treating them with an acid in a lower alkanol or by the use of ion exchange resins to form the required salt either directly from the compound in the base form from a different addition salt.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

If a solid carrier is used, the composition can be prepared in the form of a tablet, capsule containing powder or pellets, troche or lozenge. The amount of solid carrier in a unit dosage form is generally from about 25 mg to about 300 mg. If a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring or colouring agents can also be included. The sterile liquids can be prepared in ampoules, multidose vials or unit dose disposable systems. The preparation can also be in a semi-solid form, for example a cream, paste, ointment or gel, or in a liquid or aerosol form for topical application. The pharmaceutical compositions are prepared by conventional techniques involving procedures such as milling, mixing, granulating and compressing, spray drying, freeze drying or dissolving or dispersing the ingredients as appropriate to the desired preparation. The active ingredient is present in the compositions in an effective amount to block histamine $H_2$-receptors. Preferably, each dosage unit contains the active ingredient in an amount of from about 50 mg to about 250 mg.

The active ingredient is preferably administered one to six times per day. The daily dosage regimen is preferably from about 150 mg to about 1,500 mg. The route of administration can be oral or parenteral.

The invention is illustrated by the following Examples in which temperatures are in °C.

EXAMPLE 1

(a) A mixture of 2-methoxy-5-cyanopyridine (61.26 g), semi-carbazide hydrochloride (76.4 g), sodium acetate (74.92 g), ethanol (1,300 ml) and water (400 ml) was hydrogenated at 344 kPa using Raney nickel catalyst (1.0 g). The mixture was evaporated to a volume of 500 ml, water (1,000 ml) was added and the mixture was allowed to stand at 0° overnight. The mixture was filtered and the solid was washed with water and dissolved in 10% hydrochloric acid (1,000 ml). Formaldehyde solution (36% w/v, 450 ml) was added and the mixture was warmed for 15 minutes, allowed to cool and was added to a solution of sodium acetate (298.5 g) in water (900 ml). This mixture was extracted with ether and the combined extracts were successively washed with aqueous potassium carbonate and water and were dried and evaporated to give 6-methoxypyridine-3-carboxaldehyde (31.5 g, 50%), m.p. 48–49°.

(b) A mixture of 6-methoxypyridine-3-carboxaldehyde (2.34 g), monoethyl malonate (4.51 g), pyridine (12 ml) and piperidine (6 drops) was heated under reflux for 5 hours and was evaporated to an oil. This oil was partitioned between ether and dilute aqueous ammonia. The ether layer was washed with water and evaporated to an oil which crystallised on standing to give ethyl 3-(6-methoxy-3-pyridyl)acrylate (2.8 g, 79%), m.p. 49–52°.

(c) Ethyl 3-(6-methoxy-3-pyridyl)acrylate (32.33 g) in ethanol (160 ml) was hydrogenated at 344 kPa and 40° using palladium-on-charcoal catalyst (5%, 0.2 g). The mixture was filtered and the filtrate was evaporated to give ethyl 3-(6-methoxy-3-pyridyl)propionate (32.7 g) as an oil.

(d) A mixture of ethyl 3-(6-methoxy-3-pyridyl)propionate (32.74 g) and ethyl formate (17.22 g) was added dropwise over 1.5 hours to a stirred suspension of sodium hydride in oil (50%, 9.38 g) in 1,2-dimethoxyethane (50 ml) cooled to $-2°$, and allowed to stand overnight at room temperature. The mixture was poured on to ice and the mixture was extracted with ether (discarded), and the aqueous phase was adjusted to pH 5 with 2N sulphuric acid. An oil was precipitated and crystallised on standing to give ethyl 2-formyl-3-(6-methoxy-3-pyridyl)propionate (25.9 g, 70%), m.p. 91.5–94°. A sample recrystallised from aqueous ethanol had m.p. 93–94°.

(e) Nitroguanidine (4.7 g) was added to a solution of sodium methoxide (prepared from 1.15 g sodium) in methanol (50 ml) and the mixture was boiled under reflux for 45 minutes. Ethyl 2-formyl-3-(6-methoxy-3-pyridyl)propionate (10.7 g) was added and the mixture was refluxed for 34 hours and evaporated to a residue. This residue was dissolved in water and the solution was extracted with chloroform (subsequently discarded). The aqueous solution was adjusted to pH 5 with acetic acid, and the solid which precipitated out was filtered off to give 2-nitroamino-5-(6-methoxy-3-pyridylmethyl)-4-pyrimidone, m.p. 183.5–186°.

(f) An equimolar mixture of 2-nitroamino-5-(6-methoxy-3-pyridylmethyl)-4-pyrimidone and 2-(5-methyl-4-imidazolyl methylthio)-ethylamine was refluxed in ethanol for 18 hours. The solid which crystallised out on cooling was recrystallised from ethanol to give 2-[2-(5-methyl-4-imidazolyl methylthio)ethylamino]-5-(6-methoxy-3-pyridylmethyl)-4-pyrimidone, m.p. 197–198.5° in 63% yield.

(g) 2-[2-(5-Methyl-4-imidazolylmethylthio)ethylamino]-5-(6-methoxy-3-pyridylmethyl)-4-pyrimidone (0.55 g) in 2N hydrogen chloride in ethanol was boiled under reflux for 24 hours. The mixture was evaporated to dryness and the residue was recrystallised from 2-propanol/ethanol containing hydrogen chloride to give 2-[2-(5-methyl-4-imidazolylmethylthio)ethylamino]-5-(6-hydroxy-3-pyridylmethyl)-4-pyrimidone trihydrochloride, m.p. 205–209° in 71% yield.

EXAMPLE 2

(a) An equimolar mixture of 2-nitroamino-5-(6-methoxy-3-pyridylmethyl)-4-pyrimidone and 2-(2-thiazolylmethylthio) ethylamine was refluxed in ethanol for 18 hours. The solid which crystallised out on cooling was recrystallised from ethanol to give 2-[2-(2-thiazolylmethylthio)ethylamino]-5-(6-methoxy-3-pyridylmethyl)-4-pyrimidone, m.p. 95–97° in 60% yield.

(b) 2-[2-(2-Thiazolylmethylthio)ethylamino]-5-(6-methoxy-3-pyridylmethyl)-4-pyrimidone in 2N hydrogen chloride in ethanol was boiled under reflux for 24 hours. The mixture was evaporated to dryness and the residue was recrystallised from 2-propanol/ethanol containing hydrogen chloride to give 2-[2-(2-thiazolylmethylthio)ethylamino]-5-(6-hydroxy-3-pyridylmethyl)-4-pyrimidone trihydrochloride, m.p. 200–204°.

EXAMPLE 3

(a) Sodium (20.8 g) was dissolved in methanol (285 ml), a solution of 2-chloro-4-cyanopyridine (115.53 g) in methanoldioxan (1:1, 850 ml) was added and the mixture was boiled under reflux for 2½ hours and was allowed to cool. The mixture was filtered and the volume of the filtrate was reduced by evaporation in 200 ml and water (400 ml) was added. The solid which precipitated out was filtered off to give 2-methoxy-4-cyanopyridine (57.2 g, 51%), m.p. 93–95.5°.

(b) A mixture of 2-methoxy-4-cyanopyridine (57.2 g), semicarbazide hydrochloride (71.24 g), sodium acetate (69.86 g), ethanol (1,200 ml) and water (370 ml) was hydrogenated at 344 kPa using Raney nickel catalyst (1.0 g). The mixture was evaporated to a volume of 450 ml, water (900 ml) was added and the mixture was allowed to stand at 0° overnight. The mixture was filtered and the solid was washed with water and was dissolved in 10% hydrochloric acid (950 ml). Formaldehyde solution (36% w/v, 420 ml) was added and the mixture was warmed for 30 minutes, allowed to cool and was added to a solution of sodium acetate (280 g) in water (840 ml). The mixture was extracted with ether (3×500 ml) and the combined extracts were successively washed with aqueous potassium carbonate and water and were dried out evaporated to give 2-methoxypyridine-4-carboxaldehyde (20.53 g, 35%) m.p. 33–5°.

A sample recrystallised from petroleum ether had m.p. 33–36°.

(c) Substitution of 2-methoxypyridine-4-carboxaldehyde for 6-methoxypyridine-3-carboxaldehyde in the general procedure of Example 1 (b,c,d) gave ethyl 2-formyl-3-(2-methoxy-4-pyridyl)propionate as an oil, and treatment of this with nitroguanidine and sodium methoxide according to the procedure of Example 1(e) gave 2-nitroamino-5-2-methoxy-4-pyridylmethyl)-4-pyrimidone in 59% yield, m.p. 194–195.5° (from aqueous acetic acid).

(d) An equimolar mixture of 2-nitroamino-5-(2-methoxy-4-pyridylmethyl)-4-pyrimidone and 2-(5-methyl-4-imidazolyl methylthio)ethylamine was heated under reflux in ethanol for 18 hours. The solid which crystallised out on cooling was recrystallised from methanol to give 2-[2-(5-methyl-4-imidazolylmethylthio)ethylamino]-5-(2-methoxy-4-pyridylmethyl)-4-pyrimidone, m.p. 177–178° in 51% yield. The latter compound was heated under reflux in 2N hydrogen chloride in ethanol for 24 hours and the mixture was evaporated to dryness. The residue was recrystallised from 2-propanol/ethanol containing hydrogen chloride to give 2-[2-(5-methyl-4-imidazolylmethylthio)ethylamino]-5-(2-hydroxy-4-pyridylmethyl)-4-pyrimidone trihydrochloride, m.p. 172–176°.

EXAMPLE 4

An equimolar mixture of 2-nitroamino-5-(2-methoxy-4-pyridylmethyl)-4-pyrimidone and 2-(2-thiazolylmethylthio) ethylamine was heated under reflux in ethanol for 18 hours. The solid which crystallised out on cooling was purified by column chromatography on silica gel and recrystallisation from 2-propanol-ethanol to give 2-[2-(2-thiazolylmethylthio)ethylamino]-5-(2-methoxy-4-pyridylmethyl)-4-pyrimidone, m.p. 105.5–106.5° in 41% yield. The latter compound was heated under reflux in 2N hydrogen chloride in ethanol for 24 hours to give 2-[2-(2-thiazolylmethylthio)ethylamino]-5-(2-hydroxy-4-pyridylmethyl)-4-pyrimidone monohydrochloride, m.p. 169–173°.

EXAMPLE 5

Reaction of 2-(3-bromo-2-pyridylmethylthio)ethylamine with 1.15 molar equivalents of 2-nitroamino-5-(2-methoxy-4-pyridylmethyl)-4-pyrimidone in refluxing ethanol for 18 hours gave 2-[2-(3-bromo-2-pyridylmethylthio)ethylamino]-5-(2-methoxy-4-pyridylmethyl)-4-pyrimidone m.p. 70–72° which was boiled under reflux in ethanol containing hydrogen chloride to give 2-[2-(3-bromo-2-pyridylmethylthio) ethylamino]-5-(2-hydroxy-4-pyridylmethyl)-4-pyrimidone trihydrochloride, m.p. 195–198.5°.

EXAMPLE 6

(a) Substitution of 4-methoxypyridine-2-carboxaldehyde for 6-methoxypyridine-3-carboxaldehyde in the procedure of Example 1(b)(c) gave ethyl 3-(4methoxy-2-pyridyl)propionate as an oil which was formylated with ethyl formate and sodium hydride in 1,2-dimethoxyethane and reacted with nitroguanidine and sodium ethoxide to give 2-nitroamino-5-(4-methoxy-2-pyridylmethyl)-4-pyrimidone, m.p. 196–198° (decomp) (from ethanol-acetic acid).

(b) Reaction of 2-nitroamino-5-(4-methoxy-2-pyridylmethyl)-4-pyrimidone with 1.06 molar equivalents of 2-(5-methyl-4-imidazolylmethylthio)ethylamine in refluxing ethanol for 24 hours gave 2-[2-(5-methyl-4- imidazolylmethylthio)ethylamino]-5-(4-methoxy-2-pyridylmethyl)-4-pyrimidone, m.p. 128–130° (from 2-propanol).

(c) A mixture of 2-[2-(5-methyl-4-imidazolylmethylthio) ethylamino]-5-(4-methoxy-2-pyridylmethyl)-4-pyrimidone (0.97 g) and aqueous hydrobromic acid (48%, 20 ml) was boiled under reflux for 20 hours and evaporated to dryness. The residue was recrystallised from a mixture of ethanol and 2-propanol to give 2-]2-(5-methyl-4-imidazolylmethylthio) ethylamino]-5-(4-hydroxy-2-pyridylmethyl)-4-pyrimidone trihydrobromide, m.p. 167–169°. On recrystallisation from a mixture of ethanol and 2-propanol the melting point of the sample was lower owing to loss of hydrogen bromide.

EXAMPLE 17

Substitution of 4-(3-methoxy-3-pyridyl)butylamine for 2-(5-methyl-4-imidazolymethylthio)ethylamine in the procedure of Example 3(d) gave 2-[4-(3-methoxy-2-pyridyl) butylamino]-5-(2-methoxy-4-pyridylmethyl)-4-pyrimidone, m.p. 72–74° (from aqueous 2-propanol) which was heated under reflux in 2N hydrogen chloride in ethanol to give 2-[4-(3-methoxy-2-pyridyl)-butylamino]-5-(2-hydroxy-4-pyridylmethyl)-4-pyrimidone trihydrochloride m.p. 168–171°.

EXAMPLES 8 to 10

Substitution of
(i) 4-(2-pyridyl)butylamine
(ii) 4-(3-chloro-2-pyridyl)butylamine
(iii) 4-(3-bromo-2-pyridyl)butylamine
for 2-(5-methyl-4-imidazolylmethylthio)ethylamine in the procedure of Example 3(d) gives 8. 2-[4-(2pyridyl)butylamino]-5-(2hydroxy-4-pyridylmethyl)-4-pyrimidone
9. 2-[4-(3-chloro-2-pyridyl)butylamino]-5-(2-hydroxy-4-pyridylmethyl)-4-pyrimidone
10. 2-[4-(3-bromo-2-pyridyl)butylamino]-5-(2-hydroxy-4-pyridylmethyl)-4-pyrimidone as trihydrochloride salts

EXAMPLES 11 to 14

Substitution of
(i) 4-(2-pyridyl)butylamine
(ii) 4-(3-methoxy-2-pyridyl)butylamine
(iii) 4-(3-chloro-2-pyridyl)butylamine
(iv) 4-(3-bromo-2-pyridyl)butylamino
for 2-(5-methyl-4-imidazolylmethylthio)ethylamine
(a) in the procedure of Example 1(f) (g) gives
(i) 2-[4-(2-pyridyl)butylamino]-5-(6-hydroxy-3-pyridylmethyl)-4-pyrimidone
(ii) 2-[4-(3-methoxy-2-pyridyl)butylamino]-5-(6-hydroxy-3-pyridylmethyl)-4-pyrimidone
(iii) 2-[4-(3-chloro-2-pyridyl)butylamino]-5-(6-hydroxy-3-pyridylmethyl)-4-pyrimidone
(iv) 2-[4-(3-bromo-2-pyridyl)butylamino]-5-(6-hydroxy-3-pyridylmethyl)-4-pyrimidone
(b) in the procedure of Example 6(b)(c) gives
11. 2-[4-(2-pyridyl)butylamino]-5-(4-hydroxy-2-pyridylmethyl)-4-pyrimidone
12. 2-[4-(3-methoxy-2-pyridyl)butylamino]-5-(4-hydroxy-2-pyridylmethyl)-4-pyrimidone
13. 2-[4-(3-chloro-2-pyridyl)butylamino]-5-(4-hydroxy-2-pyridylmethyl)-4-pyrimidone
14. 2-[4-(3-bromo-2-pyridyl)butylamino]-5-(4-hydroxy-2-pyridylmethyl)-4-pyrimidone as trihydrobromide salts.

EXAMPLES 15 and 16

Substitution of 5,6-dimethoxypyridine-3-carboxaldehyde for 6-methoxypyridine-3-carboxaldehyde in the procedure of Example 1(b)–(e) gives 2-nitroamino-5-(5,6-dimethoxy-3-pyridylmethyl)-4-pyrimidone and this is reacted with 2-(5-methyl-4-imidazolylmethylthio)ethylamine or 4-(3-chloro-2-pyridyl)butylamine and the product heated under reflux in 2N hydrogen chloride in ethanol to give 15. 2-[2-(5-methyl-4-imidazolylmethylthio)ethylamino]-5-(6-hydroxy-5-methoxy-3-pyridylmethyl)-4-pyrimidone and
26. 2-[4-(3-chloro-2-pyridyl)butylamino]-5-(6-hydroxy-5-methoxy-3-pyridylmethyl)-4-pyrimidone as trihydrochloride salts.

EXAMPLE 17

Preparation of pharmaceutical composition for oral administration:

A pharmaceutical composition is prepared containing:

|   |   | % w/w |
|---|---|---|
| A | 2-[4-(3-chloro-2-pyridyl)butylamino]-5-(2-hydroxy-4-pyridylmethyl)-4-pyrimidone trihydrochloride | 55 |
|   | Dibasic calcium phosphate dihydrate | 20 |
|   | Approved colouring agent | 0.5 |
|   | Polyvinylpyrrolidone | 4.0 |
|   | Microcrystalline cellulose | 8.0 |
| B | Maize starch | 8.0 |
|   | Sodium starch glycollate | 4.0 |
|   | Magnesium stearate | 0.5 | by mixing together the ingredients A (substituting lactose or microcrystalline cellulose for dibasic calcium phosphate dihydrate if desired), adding a concentrated solution of polyvinylpyrrolidone, and granulating, drying and screening the dried granules; adding the ingredients B to the dried granules and compressing the mixture into tablets, containing 128, 192 or 256 mg of active ingredient (corresponding to 100, 150, and 200 mg of the free base).

EXAMPLE 18

Preparation of pharmaceutical composition for oral administration:

A pharmaceutical composition is prepared containing:

|   |   | % w/w |
|---|---|---|
| A | 2-[4-(3-bromo-2-pyridyl)butylamino]-5-(2-hydroxy-4-pyridylmethyl)-4-pyrimidone trihydrochloride | 55 |
|   | Dibasic calcium phosphate dihydrate | 20 |
|   | Approved colouring agent | 0.5 |
|   | Polyvinylpyrrolidone | 4.0 |
|   | Microcrystalline cellulose | 8.0 |
| B | Maize starch | 8.0 |
|   | Sodium starch glycollate | 4.0 |
|   | Magnesium stearate | 0.5 | by mixing together the ingredients A (substituting lactose or microcrystalline cellulose for dibasic calcium phosphate dihydrate if desired), adding a concentrated solution of polyvinylpyrrolidone, and granulating, drying and screening the dried granules; adding the ingredients B to the dried granules and compressing the mixture into tablets, containing 125, 188, or 250 mg of active ingredient (corresponding to 100, 150 and 200 mg of the free base).

EXAMPLE 19

Preparation of pharmaceutical composition for topical administration:

A pharmaceutical composition is prepared containing:

|   |   | % w/w |
|---|---|---|
| A | Stearyl alcohol | 15.0 |
|   | Beeswax | 8.0 |
|   | Sorbitan monooleate | 1.25 |
|   | Polyoxyethylene sorbitan monooleate | 3.75 |
| B | 2-[4-(3-chloro-2-pyridyl)butylamino]-5-(2-hydroxy-4-pyridylmethyl)-4-pyrimidone trihydrochloride | 1.0 |
|   | Sorbitol solution B.P. | 7.5 |
|   | Citric acid | 0.2 |
|   | Sodium citrate | 0.05 |
|   | Methylparaben | 0.18 |
|   | Propylparaben | 0.02 |
|   | Water | to 100 |

A mixture of the ingredients A is heated to 72° and added with stirring to a mixture of the ingredients B at 70°, and the stirring is continued until a cream is formed.

EXAMPLE 20

Preparation of pharmaceutical composition for topical administration:

A pharmaceutical composition is prepared containing:

|   |   | % w/w |
|---|---|---|
| A | Stearyl alcohol | 15.0 |
|   | Beeswax | 8.0 |
|   | Sorbitan monooleate | 1.25 |
|   | Polyoxyethylene sorbitan monooleate | 3.75 |
| B | 2-[4-(3-bromo-2-pyridyl)butylamino]-5-(2-hydroxy-4-pyridylmethyl)-4-pyrimidone tetrahydrochloride | 1.0 |
|   | Sorbitol solution B.P. | 7.5 |
|   | Citric acid | 0.2 |
|   | Sodium citrate | 0.05 |
|   | Methylparaben | 0.18 |
|   | Propylparaben |  |
|   | Water | to 100 |

A mixture of the ingredients A is heated to 72° and added with stirring to a mixture of the ingredients B at 70°, and the stirring is continued until a cream is formed.

Similarly, other compounds of this invention, for example the compounds of any of Examples 1–8 or 11–16, can be formulated into pharmaceutical compositions by the procedures described above in Examples 17 to 20.

We claim:

1. A pyrimidone of Structure (1):

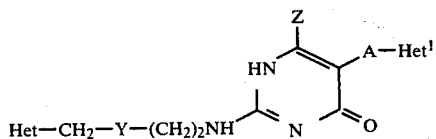

(1)

in which Het is a 2- or 4-imidazolyl group optionally substituted by lower alkyl, halogen, trifluoromethyl or hydroxymethyl, a 2-pyridyl group optionally substituted by one or more lower alkyl, lower alkoxy, halogen, amino or hydroxy groups, a 2-thiazolyl group, a 3-isothiazolyl group optionally substituted by chlorine or bromine, a 3-(1,2,5)-thiadiazolyl group optionally substituted by chlorine or bromine, or a 2-(5-amino-1,3,4-thiadiazolyl) group; Y is sulphur or methylene; Z is hydrogen or lower alkyl; A is $C_1$–$C_5$ alkylene; and $Het^1$ is 4-hydroxy-2-pyridyl, 6-hydroxy-3-pyridyl, 2-hydroxy-4-pyridyl, 4-hydroxy-5-methyl-2-pyridyl, 6-hydroxy-5-methyl-3-pyridyl, 2-hydroxy-6-methyl-4-pyridyl or 6-hydroxy-5-methoxy-3-pyridyl, in the form of the free base or a pharmaceutically acceptable acid addition salt thereof.

2. A compound according to claim 1 in which Het is a 5-methyl-4-imidazolyl, 5-bromo-4-imidazolyl, 2-pyridyl, 3-methyl-2-pyridyl, 3-methoxy-2-pyridyl, 3-ethoxy-2-pyridyl, 3,4-dimethoxy-2-pyridyl, 3-fluoro-2-pyridyl, 3-chloro-2-pyridyl, 3-bromo-2-pyridyl, 3-iodo-2-pyridyl, 3-bromo-4-methyl-2-pyridyl or 2-thiazolyl group.

3. A compound according to claim 1 in which Z is hydrogen.

4. A compound according to claim 1 in which A is methylene.

5. A compound according to claim 1 selected from
 (a) 2-[2-(5-methyl-4-imidazolylmethylthio)ethylamino]-5-(6-hydroxy-3-pyridylmethyl)-4-pyrimidone,
 (b) 2-[2-(2-thiazolylmethylthio)ethylamino]-5-(6-hydroxy-3-pyridylmethyl)-4-pyrimidone,
 (c) 2-[2-(5-methyl-4-imidazolylmethylthio)ethylamino]-5-(2-hydroxy-4-pyridylmethyl)-4-pyrimidone,
 (d) 2-[2-(2-thiazolylmethylthio)ethylamino]-5-(2-hydroxy-4-pyridylmethyl)-4-pyrimidone,
 (e) 2-[2-(3-bromo-2-pyridylmethylthio)ethylamino]-5-(6-hydroxy-4-pyridylmethyl)-4-pyrimidone,
 2-[2-(5-methyl-4-imidazolylmethylthio)ethylamino]-5-(4hydroxy-2-pyridylmethyl)-4-pyrimidone, 6. A compound according to claim 1 in which $Het^1$ is 4-hydroxy-2-pyridyl, 6-hydroxy-3-pyridyl or 2-hydroxy-4-pyridyl.

7. The compound of claim 1, said compound being 2-[2-(3-bromo-2-pyridylmethylthio)ethylamino]-5-(2-hydroxy-4-pyridylmethyl)-4-pyrimidone.

8. The compound of claim 1, said compound being 2-[4-(3-methoxy-2-pyridyl)butylamino)-5-(2-hydroxy-4-pyridylmethyl)-4-pyrimidone.

9. The compound of claim 1, said compound being 2-[4-(3-chloro-2-pyridyl)butylamino]-5-(2-hydroxy-4-pyridylmethyl)-4-pyrimidone.

10. The compound of claim 1, said compound being 2-[4-(3-bromo-2-pyridyl)butylamino]-5-(2-hydroxy-4-pyridylmethyl)-4-pyrimidone.

11. A pharmaceutical composition characterised in that it comprises a compound according to claim 1 and a pharmaceutically-acceptable carrier or diluent.

12. A method of simultaneously blocking histamine $H_1$- receptors and histamine $H_2$- receptors which comprises administering to an animal a compound of claim 1.

13. A method of blocking histamine $H_2$- receptors which comprises administering to an animal a compound of claim 1.

* * * * *